(12) United States Patent
Fujita

(10) Patent No.: US 6,486,285 B2
(45) Date of Patent: Nov. 26, 2002

(54) WATER-SWELLABLE POLYMER GEL AND PROCESS FOR PREPARING THE SAME

(75) Inventor: Akio Fujita, Kurashiki (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/767,227

(22) Filed: Jan. 23, 2001

(65) Prior Publication Data

US 2001/0018464 A1 Aug. 30, 2001

(30) Foreign Application Priority Data

Jan. 24, 2000 (JP) ........................................ 2000-014626

(51) Int. Cl.⁷ .............................................. C08G 12/06
(52) U.S. Cl. ...................... 527/312; 521/64; 521/84.1; 521/94; 521/97; 521/182; 521/184; 521/185; 521/187; 521/189
(58) Field of Search ........................... 521/64, 84.1, 94, 521/97, 182, 184, 185, 187, 189; 527/312

(56) References Cited

FOREIGN PATENT DOCUMENTS

| | | |
|---|---|---|
| GB | 962483 | 7/1964 |
| JP | 63-056501 | 3/1988 |
| JP | 2-138346 | 5/1990 |
| JP | 6-069490 | 9/1994 |
| JP | 8-508933 | 9/1996 |
| JP | 9-278803 | 10/1997 |
| JP | 11-509256 | 8/1999 |

OTHER PUBLICATIONS

S.B. Mohamed, et al., Food Chemistry, vol. 13, pps. 241–255, "Ability of Various Proteins to Form Thermostable Gels with Propylene Glycol Alginate," 1984.

J.S. McKay, et al., Carbohydrate Polymers, vol. 5, pp. 223–236, "A Comparison of the Reactivity of Alginate and Pectate Esters with Gelatin," 1985.

*Primary Examiner*—John M. Cooney, Jr.
(74) *Attorney, Agent, or Firm*—Oblon, Spivak, McClelland, Maier & Neustadt, P.C.

(57) ABSTRACT

A water-swellable polymer gel prepared by reacting an ester of a carboxyl group-containing polysaccharide with a compound having at least two α-amino groups, which is derived from a natural amino acid, and a foamed article thereof. The water-swellable polymer gel can be used in the fields such as industry, agriculture, food and medicine. The applications of the water-swellable gel in the medical field include wound dressings, adhesion-preventing materials, dialysis membranes, hemostatic materials, adhesive materials, sealants, contact lenses, materials for tissue regeneration, microcapsule materials and drug delivery systems.

16 Claims, No Drawings

WATER-SWELLABLE POLYMER GEL AND PROCESS FOR PREPARING THE SAME

BACKGROUND OF THE INVENTION

1. Field of the Invention

The present invention relates to a water-swellable polymer gel and a process for preparing the water-swellable polymer gel. More particularly, the present invention relates to a water-swellable polymer gel which is excellent in safety for human bodies, water absorbability, transparency and mechanical properties, and a process for preparing the same.

2. Discussion of the Related Art

A water-swellable hydrogel obtained by chemically crosslinking a polysaccharide has been widely utilized in the fields such as industry, agriculture, food and medicine. The applications of the water-swellable gel in the medical field include, for instance, wound dressings, adhesion-preventing materials, dialysis membranes, hemostatic materials, adhesive materials, sealants, contact lenses, materials for tissue regeneration, microcapsule materials, drug delivery systems (DDS), and the like.

The chemical crosslinking of the polysaccharide can be carried out by a chemical reaction, e.g. gelation with a polyfunctional reagent; crosslinking using a coordinate bond, e.g. gelation by calcium ions of alginic acid; crosslinking using a hydrophobic bond, e.g. gelation by heating methyl cellulose or hydroxypropyl cellulose; crosslinking using intermolecular association, e.g. cooling of agar or carrageenan to cause the gelation, or the like. Among them, the crosslinking by a chemical reaction has an advantageous merit in that water absorbability and strength of the resulting polysaccharide gel can be easily controlled depending upon its purposes.

The crosslinking of the polysaccharide by a chemical reaction can be carried out by treating a polysaccharide solution with a crosslinking reagent having at least two functional groups. However, there are some defects in the crosslinking such that the crosslinking cannot be efficiently progressed in water, because many of the polysaccharides are substantially dissolved only in water.

As a process for crosslinking a polysaccharide by a chemical reaction, there has been known a process comprising crosslinking a polysaccharide with a bifunctional low-molecular weight reagent in an aqueous solvent (hereinafter simply referred to as "low-molecular weight crosslinking agent process"). Among them, as a process for crosslinking a water-soluble polysaccharide by a chemical reaction, there have been known a process comprising crosslinking a polysaccharide with an epoxy compound in an aqueous, acidic or basic solution (Japanese Examined Patent Publication No. Hei 6-69490 and Japanese Unexamined Patent Publication No. Hei 11-509256); a process comprising crosslinking a polysaccharide with divinyl sulfone in an aqueous basic solution (Japanese Patent Laid-Open No. Hei 2-138346), and the like.

However, there are some defects in the low-molecular weight crosslinking process such that the resulting gel is extremely brittle, while the gel tends to exhibit a relatively high water absorption, and that there is necessitated a complicated procedure for thoroughly washing the polymer gel after its preparation in order to remove a crosslinking agent and a catalyst remaining in large amounts in the internal of the gel.

Therefore, the low-molecular weight crosslinking agent process cannot be necessarily considered to be a useful process from the viewpoints of physical properties and productivity of the hydrogel.

Recently, there has been developed a process comprising crosslinking a polysaccharide with a polyfunctional high-molecular weight crosslinking agent (hereinafter simply referred to as "high-molecular weight crosslinking agent process").

As the high-molecular weight crosslinking agent process, there have been known a process comprising crosslinking an ester of a carboxyl group-containing polysaccharide, for instance, propylene glycol alginate (hereinafter simply referred to as "PGA"), with a water-soluble polymer having amino group such as gelatin to cause insolubilization as disclosed in British Patent No. 962483; Japanese Unexamined Patent Publication No. Hei 8-508933; S. B. Mohamed and G. Stainsby, *Food Chemistry*, 13, 241 (1984); J. E. McKay, G. Stainsby, E. L. Wilson, *Carbohyd. Polym.*, 5, 223 (1985), and the like.

According to the above-mentioned process, it is thought that the gelation is caused via the aminolysis (amidation) of ε-amino group derived from lysine residue of a polyamino acid (protein) with an ester moiety of the PGA in water.

However, there are some defects in the gel made from PGA and a protein such as gelatin, such that water absorbability of the gel is low, because a protein solution having a high concentration is required for the preparation of the gel, so that a large amount of the protein is inevitably contained in the gel. In addition, there is also a defect in this gel such that the gel cannot be formed in a neutral aqueous solution which is suitable for materials for medical use.

Also, it has been proposed that a synthetic high-molecular weight compound having amino groups as repeating units, such as a polyethyleneimine, is used as a crosslinking agent for the PGA as disclosed in British Patent No. 962483. However, this process necessitates a treatment with a basic substance for the formation of a gel. Therefore, there are some defects in this process that pinholes are apt to be generated in the resulting gel, as well as some practical problems that the water absorbability and strength of the gel are remarkably low.

An object of the present invention is to provide a water-swellable polymer gel having high water absorbability and gel strength, the essential component of which comprises a natural ingredient, and a foam of a water-swellable polymer gel.

Another object of the present invention is to provide a process for readily preparing a water-swellable polymer gel in an aqueous solvent in high productivity and safety for human bodies.

These and other objects of the present invention will be apparent from the following description.

SUMMARY OF THE INVENTION

According to the present invention, there is provided a water-swellable polymer gel prepared by reacting an ester of a carboxyl group-containing polysaccharide with a compound having at least two α-amino groups, which is derived from a natural amino acid, and a foam made thereof.

In addition, the present invention provides a process for preparing a water-swellable polymer gel, comprising reacting an ester of a carboxyl group-containing polysaccharide with a compound having at least two α-amino groups, which is derived from a natural amino acid.

DETAILED DESCRIPTION OF THE INVENTION

The ester of a carboxyl group-containing polysaccharide (hereinafter simply referred to as "esterified polysaccharide") means a compound formed by bonding at least one of the carboxyl groups of the carboxyl group-containing polysaccharide, preferably at least two of the carboxyl groups of the carboxyl group-containing polysaccharide, with hydroxyl groups of an alcohol to form ester bonds. Among the esterified polysaccharides, those substantially water-soluble are preferable.

The alcohol includes aliphatic alcohols, aromatic aliphatic alcohols, cyclic aliphatic alcohols and heterocyclic alcohols. Among them, in consideration of the water-solubility of the esterified polysaccharide, there can be cited, for instance, aliphatic alcohols having 1 to 16 carbon atoms such as methanol, ethanol and propanol; and polyhydric alcohols having at least two hydroxyl groups and 2 to 16 carbon atoms such as ethylene glycol, propylene glycol and glycerol. As to the polyhydric alcohol, it is required that only one of hydroxyl groups of the polyhydric alcohol forms an ester bond together with carboxyl group of the carboxyl group-containing polysaccharide.

The carboxyl group-containing polysaccharide includes, for instance, carboxyl group-containing polysaccharides, such as alginic acid, xanthane gum, gellan gum, hyaluronic acid, and their physiologically acceptable artificial derivatives; artificial derivatives of polysaccharides which do not usually have any carboxyl groups, such as carboxymethyl cellulose, carboxymethyl dextran and carboxymethyl pullulan; chitin or chitosan derivatives into which carboxyl groups are introduced, such as partially maleylated chitosan, partially succinylated chitosan, carboxymethyl chitosan and carboxymethyl chitin; and the like. Among them, alginic acid and hyaluronic acid are preferable, from the viewpoint of safety for human bodies and decomposability in human bodies.

Processes for preparing an esterified polysaccharide includes, for instance, a general process described in *Jikken Kagaku Koza* 22, *Yuki Gosei IV—San, Aminosan, Pepuchido* (*Experimental Chemistry Lecture* 22, *Organic Synthesis IV—Acids, Amino Acids, Peptides*), Fourth Edition, edited by Nippon Kagaku Kai, published by Maruzen Publishing Company, 1992, 43–83; and a process described in M. Yalpani, *Tetrahedron,* 41, 2957 (1985) and the like. Particularly preferable processes include, for instance, a process of treating a carboxyl group-containing polysaccharide with an 1,2-epoxide such as ethylene oxide or propylene oxide or an 1,3-epoxide such as triethylene oxide, as disclosed in U.S. Pat. No. 2,494,912, A. B. Steiner and W. H. McNeely, *Ind. Eng. Chem.,* 43, 2073 (1951), or Japanese Patent Laid-Open No. Sho 52-36177. Kinds of the esterified polysaccharide prepared by the aforementioned process are not limited to specified ones, and any kinds can be used as long as they are within the scope of the above concept.

When the carboxyl group-containing polysaccharide is alginic acid, the esterified polysaccharide includes PGA, ethylene glycol alginate, trimethylene glycol alginate, butylene glycol alginate, pentylene glycol alginate, and the like.

When the carboxyl group-containing polysaccharide is hyaluronic acid, the esterified polysaccharide includes propylene glycol hyaluronate, ethylene glycol hyaluronate, trimethylene glycol hyaluronate, butylene glycol hyaluronate, pentylene glycol hyaluronate, and the like.

Among the esterified polysaccharides, the PGA and propylene glycol hyaluronate are preferable, from the viewpoints of safety for human bodies and decomposability in human bodies.

The compound having at least two α-amino groups, which is derived from a natural amino acid used as another essential component of the water-swellable polymer gel of the present invention (hereinafter simply referred to as "polyamine") means a compound having at least two primary or secondary amino groups, wherein the amino group is an α-amino group of an amino acid found in nature, such as alanine, glycine, phenylalanine, serine, valine, lysine or glutamic acid.

Kinds of the polyamine which can be used in the present invention are not limited to specified ones. The polysaccharides, the polyamino acids, or those derivatives are preferable in the present invention. The polyamine can be prepared by introducing a natural amino acid derivative of which functional groups are most appropriately protected into a polysaccharide, a polyamino acid or the like by chemical modification, and thereafter deprotecting the protecting groups.

Among the polyamines, ε-poly(lysine) is preferable, from the viewpoint of availability and safety for human bodies. The ε-poly(lysine) is a water-soluble polymer compound, as represented by the formula:

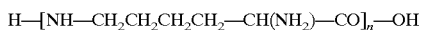

wherein n is an integer of 2 to 500, which is prepared by the condensation reaction of amino group at ε-position of lysine with carboxyl group at α-position of the lysine to form an amide bond, and α-amino group of the lysine exists on the polymer chain.

The water-swellable polymer gel of the present invention may contain at least one of other water-soluble polymers (hereinafter simply referred to as "other water-soluble polymer") as a third component other than the esterified polysaccharide and the polyamine.

Kinds of the other water-soluble polymers are not limited to specified ones. The other water-soluble polymer includes, for instance, water-soluble polysaccharides such as agarose, sodium alginate, agar, carrageenan, xanthane gum, gellan gum, dextran, hyaluronic acid, pullulan and heparin, and their physiologically acceptable artificial derivatives; chitin or chitosan derivatives, such as partially deacetylated chitin, chitosan, partially maleylated chitosan, partially succinylated chitosan and carboxymethyl chitosan; cellulose derivatives such as carboxymethyl cellulose; polyamino acids (proteins) such as collagen, atelocollagen, gelatin and casein, and their physiologically acceptable artificial derivatives, and the like.

Between the molecules of at least two other water-soluble polymers, crosslinking other than the crosslinking bond formed between the esterified polysaccharide and the polyamine can be existed. Method for forming the crosslinking includes, for instance, a method described in "Gel Handbook" (NTS, 1997), edited by Nagata and Kajiwara, or the like, that is, crosslinking of the functional groups of the water-soluble polymer, using an aldehyde compound, an epoxy compound, an isocyanate compound or the like; photo-crosslinking using a photodimerizable group or polymerizable group; crosslinking by coordination bonding with polyvalent metal ions, and the like, without intending to limit the present invention to those exemplified ones.

The water-swellable polymer gel of the present invention can further contain salts such as inorganic salts and organic salts, from the viewpoints of improving gel strength of the water-swellable polymer gel, and dispersion stability of a mixed solution containing the esterified polysaccharide and the polyamine. Examples of the salts include inorganic salts such as sodium chloride, potassium chloride, calcium chloride and sodium sulfate; and organic salts such as sodium acetate, sodium citrate and sodium succinate.

The water-swellable polymer gel of the present invention can be obtained by reacting the esterified polysaccharide with the polyamine. This reaction is an aminolysis reaction of the ester moiety of the esterified polysaccharide with α-amino group of the polyamine, namely a crosslinking reaction by amidation, as in the gel formed from the PGA and gelatin described previously.

The mixing ratio for the esterified polysaccharide and the polyamine in the reaction can be arbitrarily determined depending upon gelation time, mechanical strength and water absorbability of the polymer gel. In order to make the water-swellable polymer gel of the present invention substantially water insoluble and exhibit its high water absorbability, it is desired that the molar ratio of an ester group to α-amino group [ester group (mol)/α-amino group (mol)] is 1 to 100. The higher its molar ratio is, the higher the water absorbability of the water-swellable polymer gel becomes.

The processes for reacting the esterified polysaccharide with the polyamine to cause gelation include a process comprising reacting the esterified polysaccharide with the polyamine in solution states to cause gelation; a process comprising immersing or dipping an esterified polysaccharide in the solution of the polyamine and reacting them with each other to cause gelation; a process comprising immersing or dipping a polyamine in the solution of the esterified polysaccharide and reacting them with each other to cause gelation; and the like. The temperature during the reaction is not limited to specified ones, and can be freely controlled.

As a solvent for dissolving the esterified polysaccharide and the polyamine, water is preferable. However, an aqueous solvent prepared by adding an organic solvent to water can be used for the purpose of controlling the gelation speed or the like. Examples of the organic solvent include, for instance, alcohols such as methanol, ethanol, isopropanol, ethylene glycol and propylene glycol; ether solvents such as tetrahydrofuran and dioxane; amide solvents such as dimethylformamide, dimethylacetamide and N-methylpyrrolidone; ketone solvents such as acetone and methyl ethyl ketone; dimethyl sulfoxide, and the like. The mixing ratio of the organic solvent to water is not limited to specified ones, and can be arbitrarily determined.

In addition, pH of the solution of the esterified polysaccharide and the polyamine can be appropriately adjusted, so that gelation can be carried out under mild conditions or rapidly. When adjusting the pH, there can be used, for instance, an acidic substance such as hydrochloric acid or acetic acid; a basic substance such as sodium hydroxide; or a buffer such as phosphate buffer or borate buffer as a pH regulator.

By reacting the esterified polysaccharide with the polyamine as described above, the water-swellable polymer gel can be obtained.

The water-swellable polymer gel of the present invention can be appropriately formed into a shape depending upon its purposes. Examples of the shape include, for instance, filamentous, membraneous, tubular (hollow fibers, tubes), granular (microcapsule-like), nonwoven fabrillar, doughy, honeycomb-like, or foamed article-like (spongy), and the like. It is preferable that the water swellable polymer gel of the present invention is in the form of a foam when used for applications requiring flexibility, packability to defects, high water absorbability, and the like. This foam can be molded into filamentous, membraneous, tubular, granular, nonwoven fabrillar, doughy, honeycomb-like, or the like. Alternatively, the foam can be used by applying to, coating on, impregnating in, depositing on or embedding in other substrates and places.

Further, the water-swellable polymer gel of the present invention can be used by applying to, coating on, impregnating in, depositing on or embedding in other substrates or places. The other substrates and places include for instance, gauze, knitted fabrics, nonwoven fabrics, cotton materials, filamentous materials, films, meshes, porous sponges, rubbers, plastics, metals, artificial organs, and surface, cut surface and wounds of living tissues, and the like. Size, thickness, length, diameter, and the like of the other substrates or places are not limited to specified ones.

The molded water-swellable polymer gel can be prepared by, for instance, a process comprising extruding an esterified polysaccharide solution or a polyamine solution from a nozzle or a die or pouring the solution into a mold, thereby molding it into the aforementioned shape, and thereafter bringing the resulting molded article into contact with a polyamine solution or an esterified polysaccharide, respectively, to cause gelation; a method comprising preparing a mixed solution of an esterified polysaccharide and an polyamine, extruding the resulting mixed solution from a nozzle or a die or pouring the mixed solution into a mold, to cause gelation at the same time that the mixed solution is molded into the above-mentioned shape; and the like.

The foam of the water-swellable polymer gel of the present invention can be prepared by a general process comprising lyophilizing a gel swollen with water, or a process comprising introducing bubbles into the internal of the gel.

Examples of the process for preparing a foam comprising introducing bubbles into the internal of the gel include those processes disclosed in British Patent No. 574,382, Japanese Patent Laid-Open Nos. Hei 5-254029, 8-208868 and 8-337674 and Japanese Unexamined Patent Publication No. Hei 6-510330, and the like. When the foam of the water-swellable gel of the present invention is prepared by the above process, there can be obtained a foam of a water-swellable polymer gel having higher water absorbability and higher stability as compared to those foams disclosed in those publications.

Specific examples for the process for preparing a foam comprising introducing bubbles into the internal of the gel include a process comprising introducing bubbles into an esterified polysaccharide solution or a polyamine solution to foam, and thereafter bringing the foamed solution into contact with a polyamine solution or an esterified polysaccharide, respectively, to cause gelation; a process comprising introducing bubbles into a mixed solution of an esterified polysaccharide and a polyamine to foam, and thereafter completing its gelation.

The process comprising introducing bubbles into the solution to foam include a process comprising adding a foaming agent which generates a water-insoluble gas with heating or reaction, for instance, a decomposable blowing agent such as ammonium carbonate, azodicarbonamide, p-toluenesulfonyl hydrazide; a volatile blowing agent such as butane, hexane, an ether, or the like to foam; a process comprising mechanically stirring the solution, thereby diffusing a fed gas into the aqueous solution to foam; and the like.

The above-mentioned solution may contain an ionic or nonionic surfactant, which is a bubble-forming agent, as occasion demands, in order to stabilize the foam.

The ionic surfactant includes, for instance, anionic surfactants such as sodium stearate, sodium dodecyl sulfate, α-olefinsulfonate and sulfoalkylamides; cationic surfactants such as alkyldimethylbenzylammonium salts, alkyltrimethylammonium salts and alkylpyridinium salts; and amphoteric surfactants such as imidazoline surfactants.

The nonionic surfactant includes, for instance, polyethylene oxide alkyl ethers, polyethylene oxide alkylphenyl ethers, glycerol fatty acid esters, sorbitan fatty acid esters, sucrose fatty acid esters, and the like.

Among the surfactants, those having a low molecular weight would impart irritation and denaturing actions to a living tissue or a physiologically active substance (an enzyme or the like). Therefore, it is preferable to avoid using such a surfactant when the foam of the water-swellable polymer gel of the present invention is used in the applications for materials for medical use.

The esterified polysaccharide itself exhibits amphipatic property, so that the esterified polysaccharide functions as a bubble-forming agent for stabilizing gas-liquid interface. Accordingly, the surfactant may not be necessarily used since the esterified polysaccharide has a property for stably introducing (foaming) bubbles. Since the esterified polysaccharide has reactivity in addition to the amphipatic property, the esterified polysaccharide can be referred to as "reactive surfactant polysaccharide."

In addition, as the surfactant, there can be also used a protein such as albumen, gelatin or albumin, or lecithin.

When the above solution is foamed, the foam stability might not become sufficiently high in some cases. For instance, when the bubbles disappear before the completion of crosslinking, there can be added to this solution as a stabilizer of bubbles, a higher alcohol such as dodecyl alcohol, tetradecanol or hexadecanol; an amino alcohol such as ethanolamine; a water-soluble polymer such as carboxymethyl cellulose; and the like.

The foam can also be stabilized by adding a polysaccharide, which dissolves in water when heated and which is gelated when cooled, to the aqueous solution of the esterified polysaccharide to once cause the gelation of the entire solution. The polysaccharide includes natural polysaccharides such as agarose, agaropectin, amylose, amylopectin, arabinan, isolichenan, curdlan, agar, carrageenan, gellan gum, nigeran and laminaran.

The water-swellable polymer gel of the present invention is molded into a formed article as described above, but the process for molding is not limited to those described ones.

The polymer gel contains unreacted ester groups derived from the esterified polysaccharide and unreacted α-amino groups derived from the polyamine not participating in the amide bonding. Therefore, from the viewpoints of improvements in function and water absorbability of the polymer gel, after the esterified polysaccharide and the polyamine are reacted to form a water-swellable polymer gel, the water-swellable polymer gel is impregnated with a compound reactive with ester group or α-amino group to react the compound with the gel having unreacted ester groups or unreacted α-amino groups.

Since the α-amino group of the water-swellable polymer gel is highly reactive to various compounds, the water-swellable polymer gel can be subjected to, for instance, acylation, alkylation, formation of imine(Schiff base), reductive alkylation, or the like. The compound reactive with α-amino group includes, for instance, acid anhydrides such as acetic anhydride and succinic anhydride; aldehydes such as acetaldehyde and glyoxylic acid; alkylating agents such as alkyl halides and dimethyl sulfate; and the like, without intending to limit to those exemplified ones.

In addition, the ester group of the water-swellable polymer gel is reacted with a compound having an amino group to form amide bonding. The compound having amino group includes, for instance, ethanolamine, phosphoryl ethanolamine, taurine, amino acids, proteins and oligopeptides. It is preferable that the reaction of the water-swellable polymer gel with the compound having an amino group is carried out under basic conditions such as pH of not less than 7.

The water-swellable polymer gel of the present invention can be used as it is. Alternatively, the gel can be used after the gel is washed by immersing the gel in the aqueous solvent. In addition, the gel can be used after a part or all of the aqueous solvent is removed from the gel by means of drying with heating, drying under reduced pressure or lyophilization.

Washing the water-swellable polymer gel is an effective means for removing toxic additives and by-products when those ingredients are incorporated in the internal of the gel.

The process for drying the water-swellable polymer gel of the present invention is not limited to specified ones, and can be appropriately selected depending upon the applications of the water-swellable polymer gel. The water-swellable polymer gel can be dried after immersing the water-swellable polymer gel in a water-miscible organic solvent, for instance, an alcohol solvent such as methanol, ethanol or propanol, or an acetone solvent, thereby replacing at least a part of the aqueous solvent contained in the water-swellable polymer gel by the water-miscible organic solvent. The temperature during drying the water-swellable polymer gel is not limited to specified ones, and the temperature can be appropriately selected within the range so that the object of the present invention would not be hindered.

In order to improve flexibility of the dried water-swellable polymer gel of the present invention, a plasticizing agent can be used. The plasticizing agent includes, for instance, polyhydric alcohols such as glycerol, ethylene glycol, polyethylene glycol, sorbitol, propylene glycol and polypropylene glycol, dimethyl sulfoxide, water and the like. The plasticizing agent can be incorporated into the water-swellable polymer gel by adding the plasticizing agent to the solution before gelation, impregnating the plasticizing agent in the internal of the water-swellable polymer gel after gelation, or adding the plasticizing agent to the water-swellable polymer gel after drying the gel.

In addition to the method using the above-mentioned plasticizing agent as a method for softening the foam of the water-swellable polymer gel, there can be cited a process comprising compressing the foam of the water-swellable polymer gel into a relatively thin sheet. When the foam of the water-swellable polymer gel is compressed, since a three-dimensional supporting structure of the foam of the polymer gel is partially destroyed, it is thought that flexibility can be imparted to the gel. The compression can be carried out with a pressing machine, a roller, or the like. Also, the thickness of the foam of the water-swellable polymer gel can be controlled by the adjustment of a spacer, a gap or the like. The thickness of the foam of the water-swellable polymer gel after compression is not limited to specified ones, and the thickness can be appropriately adjusted in accordance with the applications of the water-swellable polymer gel of the present invention.

The water-swellable polymer gel of the present invention is a hydrogel material which has both high gel strength and high water absorbability. Therefore, the water-swellable polymer gel of the present invention can be applied to a wide scope of fields such as industry, agriculture, foods, medicine, and the like. Among them, the water-swellable polymer gel of the present invention can be suitably applied especially to materials for medical use, from the viewpoints of water absorbability, safety and mechanical properties.

The material for medical use includes, for instance, wound dressings, adhesion-preventing materials, dialysis membranes, hemostatic materials, adhesive materials, sealants, contact lenses, materials for tissue regeneration, microcapsule materials, drug delivery systems (DDS), and the like. The material for medical use may incorporate a physiologically active substance (for instance, heparin, dermatan sulfate, heparan sulfate, cytokine, an anti-inflammatory agent, a growth factor, an enzyme or the like), an anti-bacterial agent, a living cell, or the like.

When the wound dressing is used for the treatment of lesion such as trauma, burn or ulcer, the lesion can be treated with effectively maintaining the growth factor by applying the gel to the wound site. When the amount of exudates from the wound site is relatively large, it is preferable to use a foam of the water-swellable polymer gel in order to carry out the filling of apellous wounds, and absorbing, retaining and draining of the excess exudates.

The water-swellable polymer gel of the present invention may contain, or can be bonded to, at least one member selected from the group consisting of disinfectants, antibiotics, anti-bacterial agents, growth factors [for instance, fibroblast growth factor (FGF), epidermal growth factor (EGF), and the like], structure proteins (for instance, fibrin, collagen, and the like), and various amino acids and vitamins for the purposes of accelerating the cure of the lesion and preventing the infection of bacteria.

When the foam of the water-swellable polymer gel of the present invention is used for the above applications, it is desired that the gel is used in a state in which at least a part of water is removed. When the dried foam is softened by the compression treatment, the foam can be easily deformed along the wound, so that it is not necessarily required to contain in the foam a low molecular weight compound having eluting property, such as a plasticizing agent. Therefore, the wet environment of the wound can be maintained to a level of the original living body, so that there is little risk for inhibiting the cure of the wound.

In addition, a water-containing water-swellable polymer gel or a dried membraneous water-swellable polymer gel can be applied to a wound site in which exudates are existed in a relatively small amount. Alternatively, the water-swellable polymer gel of the present invention or its foam can be formed at the wound site.

The adhesion-preventing material is a material which prevents adhesion of a surgical wound during the surgery, so that the recovery of the wound is accelerated. The water-swellable polymer gel of the present invention can also be used as the adhesion-preventing material. In this case, the adhesion can also be prevented by pasting the water-swellable polymer gel to a site where adhesion should be prevented such as abdominal wall or intraperitoneal organs, or forming the water-swellable polymer gel in situ, thereby covering and protecting the site with the gel. The water-swellable polymer gel can be used in any forms such as films, coatings and foams. When the water-swellable polymer gel is formed in situ, its coating can be easily formed by supplying the water-swellable polymer gel to the site in the form of a liquid. Therefore, this method is particularly useful for surgeries under an endoscope or the like.

The water-swellable polymer gel of the present invention can be also used as a material for tissue regeneration, i.e. as an extracellular matrix for regeneration of skins, mucosa, bones, cartilage, blood vessels, valves, nerves, and cornea. In this case, the material for tissue regeneration may contain or can be bonded to a cell growth factor, such as FGF or BMP; a structure protein, such as fibrin or collagen; a cell adhesion molecule, such as RGD peptide; a living cell, such as hepatocyte, fibroblast, osteoblast or cartilage cell. When the water-swellable polymer gel is used as a material for tissue regeneration, the water-swellable polymer gel can be pasted to the site for regenerating the tissue, or the gel can be formed in situ. In addition, the wounded living tissue would recover by autotherapy, if the invasion of the fibrous tissue to a defective site can be prevented. Therefore, the water-swellable polymer gel of the present invention can be used as a barrier for preventing invasion of the fibrous tissue.

When the water-swellable polymer gel of the present invention is used for applications in which an adhesion-preventing material, a hemostatic material, an adhesive material, a sealant or a material for tissue regeneration is embedded in a living body, it is desired that the water-swellable polymer gel exhibits each of the functions, and thereafter is rapidly biodegraded and absorbed. Therefore, it is preferable that the esterified polysaccharide used in the water-swellable polymer gel is decomposed to low-molecular weight compounds in the living body. The esterified polysaccharide which can be suitable used for this application includes, for instance, esterified alginate, esterified hyaluronate, and the like.

It is preferable that the material for medical use made of the water-swellable polymer gel of the present invention is used after sterilization. The method for sterilization is not limited to specified ones, and any methods can be appropriately employed in accordance with the kinds of the materials for medical use. The method for sterilization includes, for instance, sterilization by autoclaving (for instance, 121° C. for 20 minutes), sterilization with ethylene oxide gas, sterilization with γ-rays, sterilization with electron beams, or the like.

As explained above, since the water-swellable polymer gel of the present invention is obtained by reacting the esterified polysaccharide with the polyamine, the gel can be efficiently formed even in an aqueous solvent near neutral pH. Also, since an ingredient derived from nature is used in the gel as raw materials, the gel is excellent in biodegradability and safety for human bodies, and moreover control of physical properties such as gelation time, water absorbability and gel strength can be facilitated. It is thought that the above advantages are derived from the fact that the basicity of the α-amino group of the polyamine is considerably lower than that of ε-amino group of lysine or an alkylamine employed in the prior art. In other words, it is deduced that the above advantages are derived from the fact that the concentration of free amino groups which can participate in crosslinking is higher in the case of α-amino group even under low pH conditions, as compared to that in the case of ε-amimo group or the alkylamine.

EXAMPLES

Next, the present invention will be described more specifically by means of the following working examples, without intending to limit the scope or spirit of the present invention to those examples.

In each of Examples and Comparative Examples, degree of swelling, viscosity and gel strength were determined in accordance with the following methods.

A. Degree of Swelling

The degree of swelling of a water-swellable polymer gel was determined by the equation:
[Degree of Swelling]

$$=[Wg1 \text{ (water-swollen gel)} - Wg2 \text{ (dried gel)}]/Wg2 \text{ (dried gel)}$$

wherein Wg1 (water-swollen gel) is a weight after immersing a dried polymer gel or a polymer gel containing an aqueous solvent in ion-exchanged water or physiological saline for not less than 4 hours; and Wg2 (dried gel) is a weight of the dried polymer gel.

B. Viscosity

The viscosity was determined by using a Brookfied viscometer. The unit for viscosity is mPa•s. The viscosity is a value determined by using a 1% by weight aqueous solution at 20° C.

C. Gel Strength

Two sheets of mesh sheets having a size of 1 cm (width)×2 cm (length) commercially available from ADVANTEC under the trade name of MESH SHEETS (76 mm) were placed at a distance of about 1 mm on a fluorocarbon resin plate having a size of 1 cm×1 cm. The amount 0.3 mL of a raw material solution for gel was widely spread over the entire plate, and the gel was formed in accordance with the method described in each of Examples and Comparative Examples. After removing the fluorocarbon resin plate, the mesh parts were clamped with a jig for autograph commercially available from Shimadzu Corporation under the trade name of EZ-test, and the maximum stress until breakage, that is, tensile strength at break was determined. This tensile strength at break was defined as gel strength.

Example 1

Preparation of PGA-ε-Poly(Lysine) Gel

To 30 g of a 2% by weight aqueous solution of PGA commercially available from Wako Pure Chemical Industries, Ltd. (viscosity: 100 mPa•s) was added 2.4 mL of a 10% by weight aqueous solution of ε-poly(lysine) commercially available from CHISSO CORPORATION, and the resulting mixed solution was thoroughly stirred.

The mixed solution was allowed to stand at room temperature in a sample bottle, to cause gradual gelation of the mixed solution. The gelation time, which is defined as a time period from the time at which the aqueous solution of PGA and the aqueous solution of ε-poly(lysine) were mixed to the time at which the mixed solution did not flow out from the sample bottle when the bottle was tilted, was about 9 minutes.

Next, the formed gel was allowed to stand at room temperature for 16 hours, and thereafter immersed in 300 mL of ion-exchanged water for 24 hours, to give a transparent polymer gel having a degree of swelling of 5.2.

Examples 2 to 4

Preparation of PGA-ε-Poly(Lysine) Gel with Controlled Water-Absorbability

To 30 g of a 2% by weight aqueous solution of PGA commercially available from Wako Pure Chemical Industries, Ltd. (viscosity: 100 mPa•s) was added 4.8 mL, 0.8 mL or 0.4 mL of a 10% by weight aqueous solution of ε-poly(lysine) commercially available from CHISSO CORPORATION, and the resulting mixed solution was thoroughly stirred in the same manner as in Example 1.

The mixed solution was allowed to stand at room temperature in a sample bottle, to cause gradual gelation of the mixed solution. The gelation time was determined in the same manner as in Example 1. The results are shown in Table 1.

Next, the formed gel was allowed to stand at room temperature for 16 hours, and thereafter immersed in 300 mL of ion-exchanged water for 24 hours, to give a water-swollen polymer gel. The gelation time and the degree of swelling of the resulting polymer gel are shown in Table 1.

TABLE 1

| Example No. | 2% by weight Aqueous Solution of PGA (g) | Amount of 10% by weight ε-Poly(Lysine) Aqueous Solution (mL) | Gelation Time (minutes) | Degree of Swelling |
|---|---|---|---|---|
| 1 | 30 | 2.4 | about 9 | 5.2 |
| 2 | 30 | 4.8 | about 5 | 2.8 |
| 3 | 30 | 0.8 | about 30 | 98.1 |
| 4 | 30 | 0.4 | about 60 | 522.4 |

It is clear from the results shown in Table 1 that the gelation time and the degree of swelling can be accurately controlled by adjusting the amount of the aqueous solution of ε-poly(lysine).

Examples 5 to 8

Preparation of PGA-ε-Poly(Lysine) Gel

A 10% by weight aqueous solution of ε-poly(lysine) was prepared by adjusting its pH to 7.5, 8.0, 8.5 or 9.0 with acetic acid.

Next, each of the previously prepared aqueous solution of ε-poly(lysine) was added in the amount of 1 mL to 10 g of a 2% by weight aqueous solution of PGA commercially available from Funakoshi Co., Ltd. (viscosity: 100 to 150 mPa•s), and the resulting mixed solution was thoroughly stirred.

The mixed solution was allowed to stand at room temperature in a sample bottle, to cause gradual gelation of the mixed solution. The gelation time was determined in the same manner as in Example 1. The results are shown in Table 2.

Next, the formed gel was allowed to stand at room temperature for 5 hours, and thereafter immersed in 300 mL of ion-exchanged water for 24 hours, to give a water-swollen transparent polymer gel. The degree of swelling of the resulting polymer gel is shown in Table 2.

TABLE 2

| Example No. | 2% by Weight Aqueous Solution of PGA (g) | 10% by Weight Aqueous Solution of ε-Poly(Lysine) | | Gelation Time (minutes) | Degree of Swelling |
|---|---|---|---|---|---|
| | | Amount (mL) | pH | | |
| 1 | 10 | 1 | 7.5 | about 70 | 119.4 |
| 2 | 10 | 1 | 8.0 | about 22 | 59.1 |
| 3 | 10 | 1 | 8.5 | about 15 | 33.7 |
| 4 | 10 | 1 | 9.0 | about 9 | 16.1 |

It is clear from the results shown in Table 2 that the gelation time and the degree of swelling can be accurately controlled by adjusting the pH of the aqueous solution of ε-poly(lysine).

Example 9

Preparation of PGA-ε-Poly(Lysine) Gel

To 50 g of a 2% by weight aqueous solution of PGA commercially available from Kibun Food Chemifa Co., Ltd.

(viscosity: about 200 mPa•s) was added 0.22 mL of a 24% by weight aqueous solution of ε-poly(lysine) of which pH was adjusted to 7.5 with acetic acid (the amount of α-amino group: 0.5 mmol).

The resulting mixed solution was allowed to stand at room temperature for 5 hours, and thereafter the gel strength was determined. As a result, the gel strength was found to be 13.7 mN. In addition, the formed gel was immersed in 300 mL of ion-exchanged water for 24 hours, to give a hydrogel having a degree of swelling of 142.9, the shape of which has been retained.

Comparative Example 1

Preparation of Alginic Acid-Butanediol Diglycidyl Ether Gel

In 19 mL of 0.5% by weight aqueous solution of NaOH was dissolved 2.5 g of alginic acid commercially available from Kimitsu Chemical Industries Co., Ltd. (viscosity: about 500 mPa•s) over a period of 16 hours. To the resulting solution was added 0.95 mL of 1,4-butanediol diglycidyl ether, and the mixed solution was allowed to harden at 50° C. for 2 hours. Thereafter, the resulting gel was washed in ion-exchanged water for 2 hours, and the gel strength of the gel was determined. As a result, the gel strength was found to be 0 mN. When the gel was immersed in ion-exchanged water, its shape could not be retained at all.

Comparative Example 2

Preparation of PGA-Gelatin Gel

A 6% by weight aqueous solution of gelatin derived from bovine bone, commercially available from Wako Pure Chemical Industries, Ltd., of which pH was adjusted to 7.5 with 0.1 M phosphate buffer was prepared.

Next, 10 mL of the previously prepared aqueous solution of gelatin was added to 10 g of a 3% by weight aqueous solution of PGA commercially available from Kibun Food Chemifa Co., Ltd. (viscosity: about 80 mPa•s), and the resulting mixed solution was thoroughly stirred. The mixed solution was allowed to harden for 5 hours. Thereafter, the gel strength of the gel was determined. As a result, the gel strength was found to be 0 mN. When this gel was immersed in ion-exchanged water, its shape could not be retained at all.

Comparative Example 3

Preparation of PGA-Polyethyleneimine Gel

A 18% by weight aqueous solution of polyethyleneimine commercially available from Aldrich (molecular weight: about 75000), of which pH was adjusted to 7.5 with acetic acid was prepared.

Next, 0.1 mL of the previously prepared polyethyleneimine solution (the amount of amino group: 0.5 mmol) was added to 50 g of a 2% by weight aqueous solution of PGA commercially available from Kibun Food Chemifa Co., Ltd. (viscosity: about 200 mPa•s). As a result, the mixed solution was clouded. The mixed solution was allowed to stand at room temperature for 5 hours, and the gel strength of the formed gel was determined. As a result, the gel strength was found to be 6.9 mN. When the gel was immersed in ion-exchanged water, its shape could not be retained at all.

The results for evaluating the gel strength (gel strength after curing for 5 hours) and the degree of swelling (degree of swelling obtained after curing for 5 hours and thereafter immersing in ion-exchanged water at room temperature for 24 hours) of the gels obtained in Example 9 and Comparative Examples 1 to 3 are shown in Table 3.

TABLE 3

| Example No. | Hydrogel | Gel Strength (mN) | Degree of Swelling |
|---|---|---|---|
| 9 | PGA-ε-Poly(Lysine) Gel | 13.7 | 142.9 |
| Comp. Ex. 1 | PGA-BDDE*[1] | 0 | Undeterminable (dissolved) |
| Comp. Ex. 2 | PGA-Gelatin | 0 | Undeterminable (dissolved) |
| Comp. Ex. 3 | PGA-Polyethyleneimine | 6.9 | Undeterminable (dissolved) |

(Note)
*[1]: 1,4-Butanediol diglycidyl ether

It is clear from the results shown in Table 3 that the water-swellable polymer gel obtained in Example 9 exhibits higher gel strength as compared to the gels of Comparative Examples 1 to 3, which are prior arts, even under water-containing state.

Example 10

Preparation of PGA-ε-Poly(Lysine) Gel Film

To 50 g of a 2% by weight aqueous solution of PGA commercially available from Kibun Food Chemifa Co., Ltd. (viscosity: about 200 mPa•s) was added a 24% by weight aqueous solution ε-poly(lysine) commercially available from CHISSO CORPORATION of which pH was adjusted to 9.5 with acetic acid, and the resulting mixed solution was thoroughly stirred. Thirty grams of the resulting mixed solution was allowed to spread over a fluorocarbon resin tray having a size of 10 cm×10 cm, and allowed to harden for 5 hours. Thereafter, the hardened coating was dried with a dryer temperature-controlled to 70° C. for 4 hours, to give a film.

The resulting dried gel film was immersed in physiological saline commercially available from Otsuka Pharmaceutical Co., Ltd. for 4 hours. As a result, the degree of swelling was found to be 34.6, and the gel strength 186.3 mN.

Comparative Example 4

Preparation of PGA-Gelatin Gel Film

A 6% by weight aqueous solution of gelatin derived from bovine bone, commercially available from Wako Pure Chemical Industries, Ltd., of which pH was adjusted to 9.5 with phosphate buffer was prepared.

Next, 2.5 mL of the previously prepared aqueous solution of gelatin was added to 10 g of a 3% by weight aqueous solution of PGA commercially available from Kibun Food Chemifa Co., Ltd. (viscosity: about 80 mPa•s), and the resulting mixed solution was thoroughly stirred. The mixed solution was allowed to stand at room temperature, to give a soft, transparent gel. Thirty grams of this solution was allowed to spread over a fluorocarbon resin tray having a size of 10 cm×10 cm, and the coating was dried with a dryer temperature-controlled to 70° C. for 4 hours, to give a film. In 100 mL of a 5% by weight aqueous potassium hydroxide was immersed 0.3 g of the resulting film for 15 seconds, and thereafter washed with ion-exchanged water. Subsequently, the film was dried at 70° C. for 2 hours, to give a PGA-gelatin gel film. The resulting dried gel film was immersed in physiological saline for 4 hours. As a result, the degree of swelling was found to be 6.0, and the gel strength 120.6 mN.

Comparative Example 5

Preparation of PGA-Polyethyleneimine Gel Film

A 19% by weight aqueous solution of polyethyleneimine commercially available from Aldrich (molecular weight: about 75000), of which pH was adjusted to 7.5 with acetic acid was prepared.

To 50 g of a 2% by weight aqueous solution of PGA commercially available from Kibun Food Chemifa Co., Ltd. (viscosity: about 200 mPa•s) was added 0.09 mL of the previously prepared polyethyleneimine solution (the amount of amino group: 0.5 mmol). As a result, the solution was clouded. Thirty grams of this solution was spread over a fluorocarbon resin tray having a size of 10 cm×10 cm, and the coating was dried with a dryer temperature-controlled to 70° C. for 4 hours, to give a film. In 100 mL of a 5% by weight aqueous potassium hydroxide was immersed 0.3 g of the resulting film for 15 seconds, and thereafter washed with ion-exchanged water. Subsequently, the film was dried at 70° C. for 2 hours, to give a PGA-polyethyleneimine gel film. The resulting dried gel film was immersed in physiological saline for 4 hours. As a result, the degree of swelling was found to be 5.7, and the gel strength 36.3 mN.

The results for evaluating the gel strength (gel strength after immersing in physiological saline at 37° C. for 4 hours) and the degree of swelling (degree of swelling obtained after immersing in physiological saline at 37° C. for 4 hours) of the gels obtained in Example 10 and Comparative Examples 4 and 5 are shown in Table 4.

TABLE 4

| Example No. | Film | Degree of Swelling | Tear Strength at Break (mN) |
| --- | --- | --- | --- |
| 10 | PGA-$\epsilon$-Poly(Lysine) | 34.6 | 186.3 |
| Comp. Ex. 4 | PGA-Gelatin | 6.0 | 120.6 |
| Comp. Ex. 5 | PGA-Polyethyleneimine | 5.7 | 36.3 |

It is clear from the results shown in Table 4 that the water-swellable polymer gel film obtained in Example 10 has higher gel strength, while having a remarkably higher degree of swelling, as compared to the gel films obtained in Comparative Examples 4 and 5.

Example 11

Preparation of κ-Carrageenan-Containing PGA-$\epsilon$-Poly(Lysine) Gel Film In 98 g of ion-exchanged water was dissolved 2 g of κ-carrageenan commercially available from Wako Pure Chemical Industries, Ltd. at 60° C., to give a 2% by weight aqueous solution of κ-carrageenan.

Next, the previously prepared aqueous solution of κ-carrageenan was mixed with 20 g of a 2% by weight aqueous solution of PGA commercially available from Funakoshi Co., Ltd. (viscosity: 100 to 150 mPa•s). Thereafter, 0.1 mL of a 26.9% by weight aqueous solution of $\epsilon$-poly(lysine) commercially available from CHISSO CORPORATION was added to the mixed solution, and 25 g of the resulting mixed solution was spread over a fluorocarbon resin tray having a size of 10 cm×10 cm, and allowed to harden at room temperature for 2 hours. Subsequently, the gel was dried with a dryer temperature-controlled to 70° C. for 2 hours, to give a dried gel film. When the dried gel film was immersed in physiological saline for 24 hours, the gel film absorbed water, and the degree of swelling was found to be 21.3.

Example 12

Preparation of PGA-$\epsilon$-Poly(Lysine) Gel Film

To 30 g of a 2% by weight aqueous solution of PGA commercially available from Funakoshi Co., Ltd. (viscosity: 100 to 150 mPa•s) was added 0.3 mL of a 26.9% by weight aqueous solution of $\epsilon$-poly(lysine) commercially available from CHISSO CORPORATION. Twenty-five grams of the resulting mixed solution was spread over a fluorocarbon resin tray having a size of 10 cm×10 cm, and allowed to harden at room temperature for 2 hours. The resulting gel was immersed for 2 hours in 50 mL of a 50% by volume aqueous ethanol solution containing 1.5 mL of acetic anhydride commercially available from Kanto Kagaku K.K. The gel was thoroughly washed with ion-exchanged water, and dried with a dryer temperature-controlled to 70° C. for 2 hours, to give a dried gel film. When the dried gel film was immersed in physiological saline for 24 hours, the gel film absorbed water, and the degree of swelling was found to be 16.3.

Example 13

Production of Foam Made of PGA-$\epsilon$-Poly(Lysine) Gel

One-hundred grams of a 1.5% by weight aqueous solution of PGA commercially available from Wako Pure Chemical Industries, Ltd. (viscosity: 80 to 120 mPa•s) was stirred with introducing the air into the aqueous solution with a beater (Kitchen-Aid mixer) for about 10 minutes to foam. To the resulting foamed solution was added 1 mL of a 26.9% by weight of aqueous solution of $\epsilon$-poly(lysine) commercially available from CHISSO CORPORATION, and the mixture was stirred with the beater for additional 5 minutes. The density of the solution at this point was 0.29 g/cm$^3$.

Next, 30 g of the foamed solution was spread over a fluorocarbon resin-coated tray having a size of 10 cm×10 cm, and allowed to stand at room temperature for 2 hours. The resulting water-absorbed foamed gel was dried at 70° C. for 3 hours, to give a 10 cm×10 cm×0.7 cm spongy, flexible foam.

In order to evaluate the water absorbability, the resulting dried foam was placed on a polyurethane sponge sufficiently containing physiological saline and allowed to stand at 37° C. to absorb water. As a result, the degree of swelling after 24 hours was about 38. In addition, the water absorbability of the dried foam sterilized by 25 kGy γ-ray irradiation was evaluated. As a result, the degree of swelling after 24 hours was about 25. The foam subjected to γ-ray irradiation sufficiently retained its shape even after water absorption, and no disintegration or dissolution of the foam was observed.

Example 14

Production of Foam Made of PGA-$\epsilon$-Poly(Lysine) Gel

One-hundred grams of a 2% by weight aqueous PGA commercially available from Wako Pure Chemical Industries, Ltd. (viscosity: 80 to 120 mPa•s) was stirred with introducing the air into the aqueous solution with a beater for about 10 minutes to foam. To the resulting foamed solution was added 0.5 mL of a 26.9% by weight of aqueous solution of ε-poly(lysine) commercially available from CHISSO CORPORATION, and the mixture was stirred with the beater for additional 5 minutes. The density of the foamed solution at this point was 0.31 g/cm$^3$.

Next, 30 g of the foamed solution was spread over a fluorocarbon resin-coated tray having a size of 10 cm×10 cm, and allowed to stand at room temperature for 2 hours. The resulting water-containing foamed gel was dried at 70° C. for 3 hours, to give a 10 cm×10 cm×0.7 cm spongy, flexible foam.

In order to evaluate the water absorbability, the foam was allowed to absorb physiological saline at 37° C. in the same manner as in Example 13. As a result, the degree of swelling after 24 hours was about 45. In addition, the water absorbability of the dried foam sterilized by 25 kGy γ-ray irradiation was evaluated. As a result, the degree of swelling after 24 hours was 38. The spongy foam sufficiently retained its shape even after water absorption, so that no disintegration or dissolution of the spongy foam was observed.

Comparative Example 6

Production of Foam Made of PGA-Polyethyleneimine Gel

A 19% by weight aqueous solution of polyethyleneimine commercially available from Aldrich (molecular weight: about 75000), of which pH was adjusted to 7.5 with acetic acid was prepared.

On the other hand, 500 g of a 2% by weight aqueous solution of PGA commercially available from Kibun Food Chemifa Co., Ltd. (viscosity: about 200 mPa•s) was stirred with introducing the air into the aqueous solution with a beater for about 10 minutes to foam. When 0.9 mL of the previously prepared aqueous polyethyleneimine solution was added to the resulting foamed solution, the foamed solution abruptly shrank, so that the density of the solution became 0.67 g/cm$^3$. Thirty grams of this foamed solution was spread over a fluorocarbon resin tray having a size of 10 cm×10 cm. The resulting foamed gel was dried with a dryer temperature-controlled to 70° C. for 2 hours.

In 100 mL of a 5% by weight aqueous potassium hydroxide solution was immersed 0.5 g of the dried gel for 15 seconds, and thereafter washed with ion-exchanged water. This gel was dried at 70° C. for 2 hours. However, the gel did not become bulky and was formed into a hard film of 10 cm×10 cm×0.3 cm. When the resulting dried gel film was allowed to absorb physiological saline at 37° C. in the same manner as in Example 13, the degree of swelling was found to be 4.3, and the gel did not substantially absorb saline.

Comparative Example 7

Preparation of Foam Made of Calcium Alginate Gel

To 100 g of a 2% by weight aqueous solution of sodium alginate commercially available from Wako Pure Chemical Industries, Ltd. (viscosity: 500 to 600 mPa•s) was added 0.1 mL of a surfactant commercially available from Nacalaitesque under the trade name of Triton X-100, and the mixture was stirred with a beater to foam. The density after stirring was 0.29 g/cm$^3$.

Next, 30 grams of the foamed solution was spread over a fluorocarbon resin tray having a size of 10 cm×10 cm. The resulting foamed gel was immersed in 100 mL of a 5% by weight aqueous calcium chloride for 12 hours, and allowed to harden. The resulting spongy gel was dried with a dryer temperature-controlled to 70° C. for 2 hours. As a result, the spongy gel was shrunk to a size of about 6 cm×6 cm×0.5 cm to form a hard sponge. When this sponge was allowed to absorb physiological saline at 37° C. in the same manner as in Example 13, the degree of swelling after 24 hours was found to be 0.7. In addition, the water absorbability of the dried foam sterilized with 25 kGy γ-ray irradiation was evaluated. As a result, the degree of swelling after 24 hours was found to be 1.5.

Comparative Example 8

Preparation of Foam Made of Calcium Alginate Gel

In 84 g of ion-exchanged water were completely dissolved 3.8 g of sodium alginate commercially available from Wako Pure Chemical Industries, Ltd. (viscosity: 100 to 150 mPa•s) and 1.9 g of sodium carbonate, and 0.5 g of calcium carbonate was added to the mixed solution, and sufficiently stirred.

On the other hand, a solution was prepared by completely dissolving 3.8 g of sodium alginate commercially available from Wako Pure Chemical Industries, Ltd. (viscosity: 100 to 150 mPa•s) in 80 g of ion-exchanged water, and thereafter adding thereto 3.6 g of acetic acid.

Twenty grams each of the two aqueous sodium alginate solutions prepared as described above were mixed, thereby resulting in abrupt foaming. Next, this foamed solution was spread over a fluorocarbon resin tray having a size of 10 cm×10 cm, and allowed to harden at room temperature for 0.5 hours. Thereafter, the resulting foamed gel was dried with a dryer temperature-controlled to 70° C. As a result, the gel did not become bulky and was formed into a hard film of about 10 cm×10 cm×0.2 cm. When the resulting film was allowed to absorb physiological saline at 37° C. in the same manner as in Example 13, the film was dissolved after 3 hours, so that its shape could not be retained.

Example 15

Production of Foam Made of PGA-ε-Poly(Lysine) Gel

To 500 g of a 2.5% by weight aqueous solution of PGA commercially available from Kibun Food Chemifa Co., Ltd. (viscosity: about 200 mPa•s) was added 2.5 g of sodium chloride, and sodium chloride was dissolved. Thereafter, the resulting solution was heated to 40° C. The solution was stirred, with introducing the air with a beater for about 5 minutes to foam.

To the foamed solution was added 1.95 mL of a 25% by weight aqueous solution of ε-poly(lysine) commercially available from CHISSO CORPORATION, and the mixture was stirred with the beater for about 1 minute. The density of the solution at this point was 0.35 g/cm$^3$. Next, 30 g of this foamed solution was spread over a fluorocarbon resin-coated tray having a size of 10 cm×10 cm, and allowed to stand at room temperature for 1 hour. The resulting water-containing foamed gel was dried at 70° C. for 4 hours, to give a spongy foam of 10 cm×10 cm×0.8 cm. This spongy foam was compressed with a pressing machine interposed with a 0.5 mm spacer, to give a flexible compressed foamed sheet.

In order to evaluate the water absorbability of the resulting compressed foamed sheet, this compressed foamed sheet was allowed to absorb physiological saline at 37° C. in the same manner as in Example 13. As a result, the degree of swelling after 24 hours was about 38. In addition, the water absorbability of the dried foam sterilized with ethylene oxide gas was evaluated. As a result, the degree of swelling after 24 hours was about 35. The foam sufficiently retained its shape even when the foam absorbed water, and no disintegration or dissolution was observed in the foam.

Test Example 1

Apellous wounds having a diameter of 6 mm were provided to a Japanese white rabbit (about 3.5 kg), two each on both ears. At that time, the wounds were made to the depth of bare cartilage. To each of the wounds was applied the foam obtained in Example 14 or the foam obtained in Comparative Example 7 as a control, each of which had a side of about 2 cm. Both of the applied foams were entirely covered with a polyurethane film commercially available from Johnson & Johnson under the trade name of Bioclusive, and the film was fixed by suture. The Japanese white rabbits were fed with a sufficient amount of water and feed at a constant temperature, and thereafter, the rabbit was sacrificed on 7th day from application, and the wounds were collected.

The tissues of the wounds were fixed and stained, and then observed with a microscope. As a result, the area where the foam obtained in Example 14 was applied, the epithelial gap was 1.8 mm, whereas the epithelial gap for the foam obtained in Comparative Example 7 was 3 mm or so.

As to the wounds to which the foam obtained in Example 14 was applied, residual dressing debris or foreign body reaction was not significant in the internal of the wound.

According to the process for preparing a water-swellable polymer gel of the present invention, a polymer gel can be inexpensively and efficiently prepared.

The water-swellable polymer gel of the present invention can be efficiently formed even in an aqueous solvent near neutral pH, and its essential component comprises a natural component. Accordingly, the gel is excellent in safety for human bodies. Moreover, since the water-swellable polymer gel is excellent in physical properties such as water absorbability and mechanical strength, it can be suitably applied in the fields of industry, agriculture, foods, medicine, and the like.

EQUIVALENT

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A water-swellable polymer gel comprising the reaction product of an ester of alginic acid or hyaluronic acid with a compound having at least two α-amino groups, which is derived from a natural amino acid.

2. The water-swellable polymer gel according to claim 1, wherein the ester of alginic acid or hyaluronic acid is propylene glycol alginate or propylene glycol hyaluronate.

3. The water-swellable polymer gel according to claim 1, wherein the compound having at least two α-amino groups is ε-poly(lysine).

4. A material for medical use comprising the water-swellable polymer gel of claim 1.

5. A foam of a water-swellable polymer gel comprising the foamed product of a water-swellable polymer gel of claim 1.

6. A material for medical use comprising the foamed product of a water-swellable polymer gel of claim 5.

7. The material for medical use according to claim 4, wherein said material is a wound dressing, an adhesion-preventing material, or a material for tissue regeneration.

8. The material for medical use according to claim 6, wherein said material is a wound dressing, an adhesion-preventing material, or a material for tissue regeneration.

9. A process for preparing a water-swellable polymer gel comprising: reacting an ester of alginic acid or hyaluronic acid with a compound having at least two α-amino groups, which is derived from a natural amino acid.

10. The process according to claim 9, wherein the ester of alginic acid or hyaluronic acid is propylene glycol alginate or propylene glycol hyaluronate.

11. The process according to claim 9, wherein the compound having at least two α-amino groups is ε-poly(lysine).

12. The water-swellable polymer according to claim 1, wherein the ester comprises an ester of alginic acid and is selected from the group consisting of propylene glycol alginate, ethylene glycol alginate, trimethylene glycol alginate, butylene glycol alginate and pentylene glycol alginate.

13. The water-swellable polymer according to claim 1, wherein the ester comprises an ester of hyaluronic acid and is selected from the group consisting of propylene glycol hyaluronate, ethylene glycol hyaluronate, trimethylene glycol hyaluronate, butylene glycol hyaluronate and pentylene glycol hyaluronate.

14. The water-swellable polymer according to claim 1, wherein the compound having at least two α-amino groups is polyamine.

15. The material for medical use according to claim 4, wherein said material is a wound dressing, an adhesion-preventing material, a dialysis membrane, a hemostatic material, an adhesive material, a sealant, a contact lens, a material for tissue regeneration, a microcapsule material, or a drug delivery system.

16. The material for medical use according to claim 6, wherein said material is a wound dressing, an adhesion-preventing material, a dialysis membrane, a hemostatic material, an adhesive material, a sealant, a contact lens, a material for tissue regeneration, a microcapsule material, or a drug delivery system.

* * * * *